United States Patent
Slate et al.

(10) Patent No.: US 9,925,336 B2
(45) Date of Patent: *Mar. 27, 2018

(54) CASSETTE FOR A HIDDEN INJECTION NEEDLE

(75) Inventors: John B. Slate, San Diego, CA (US);
Michael W. Burk, San Marcos, CA (US); Richard J. Koerner, San Diego, CA (US); Corey M. Magers, Encinitas, CA (US); Andrew C. Barnes, San Diego, CA (US)

(73) Assignee: AVANT MEDICAL CORP., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/454,531

(22) Filed: Apr. 24, 2012

(65) Prior Publication Data

US 2012/0265142 A1    Oct. 18, 2012

Related U.S. Application Data

(63) Continuation of application No. 12/123,888, filed on May 20, 2008, now Pat. No. 8,177,749.

(51) Int. Cl.
*A61M 37/00* (2006.01)
*A61M 5/20* (2006.01)
(Continued)

(52) U.S. Cl.
CPC ............... *A61M 5/20* (2013.01); *A61M 5/326* (2013.01); *A61M 2005/208* (2013.01);
(Continued)

(58) Field of Classification Search
CPC ......... Y10S 128/01; A61M 5/20; A61M 5/24; A61M 2005/2026; A61M 2005/2013;
(Continued)

(56) References Cited

U.S. PATENT DOCUMENTS 2,701,566 A    2/1950    Krug
2,565,081 A    8/1951    Maynes
(Continued)

FOREIGN PATENT DOCUMENTS

AU    2009249027 B2    8/2014
AU    2009249027 B2    8/2014
(Continued)

OTHER PUBLICATIONS

International Search Report issued for International Application No. PCT/US09/44693 filed May 20, 2009 of Slate et al.
(Continued)

*Primary Examiner* — Nathan R Price
*Assistant Examiner* — Melissa A Snyder
(74) *Attorney, Agent, or Firm* — Marshall, Gerstein & Borun LLP

(57) ABSTRACT

A system for injecting a fluid medicament into a patient includes a drive mechanism, and a cassette loaded with a pre-filled hypodermic syringe. When the cassette is loaded, the syringe is held firmly inside and the cassette can be selectively engaged with the drive mechanism. The drive mechanism has two motors. A first motor initially moves the hypodermic syringe from a position inside the cassette where its needle is concealed, to a position where the needle extends from the cassette for insertion into a patient for an injection. With the needle inserted, a second motor pushes the syringe stopper to expel a fluid medicament from the syringe. After an injection, the first motor withdraws the syringe back into concealment inside the cassette, to again firmly hold the syringe on the cassette. The cassette and syringe, in combination, can then be removed from the drive mechanism and discarded.

22 Claims, 3 Drawing Sheets

(51) Int. Cl.
*A61M 5/32* (2006.01)
*A61M 5/315* (2006.01)

(52) U.S. Cl.
CPC ............. *A61M 2005/31588* (2013.01); *A61M 2205/50* (2013.01); *A61M 2205/6045* (2013.01)

(58) Field of Classification Search
CPC .... A61M 2005/14268; A61M 2205/50; A61M 2005/31588; A61M 2005/14252; A61M 5/326; A61M 5/28
USPC .... 604/131, 187, 95.01, 195, 197, 198, 110, 604/192; 606/167
See application file for complete search history.

(56) References Cited

U.S. PATENT DOCUMENTS

| | | |
|---|---|---|
| 3,051,173 A | 8/1962 | Johnson et al. |
| 3,064,650 A | 11/1962 | Lewis |
| 3,720,211 A | 3/1973 | Kyrias |
| 3,859,996 A | 1/1975 | Mizzy et al. |
| 3,964,481 A | 6/1976 | Gourlandt et al. |
| 4,108,177 A | 8/1978 | Pistor |
| 4,231,368 A | 11/1980 | Becker |
| 4,276,879 A | 7/1981 | Yiournas |
| 4,421,107 A | 12/1983 | Estes et al. |
| 4,515,590 A | 5/1985 | Daniel |
| 4,573,975 A | 3/1986 | Frist |
| 4,613,328 A | 9/1986 | Boyd |
| 4,617,016 A | 10/1986 | Blomberg |
| 4,636,201 A | 1/1987 | Ambrose et al. |
| 4,758,227 A | 7/1988 | Lancaster, Jr. et al. |
| 4,787,893 A | 11/1988 | Villette |
| 4,790,823 A | 12/1988 | Charton et al. |
| 4,877,034 A | 10/1989 | Atkins et al. |
| 4,902,279 A | 2/1990 | Schmidtz et al. |
| 4,986,818 A | 1/1991 | Imbert et al. |
| 5,013,299 A | 5/1991 | Clark |
| 5,024,616 A | 6/1991 | Ogle, II |
| 5,034,003 A | 7/1991 | Denance |
| 5,080,104 A | 1/1992 | Marks et al. |
| 5,085,641 A | 2/1992 | Sarnoff et al. |
| 5,092,843 A | 3/1992 | Monroe et al. |
| 5,098,400 A | 3/1992 | Crouse et al. |
| 5,114,404 A | 5/1992 | Paxton et al. |
| 5,114,406 A | 5/1992 | Gabriel et al. |
| 5,176,643 A | 1/1993 | Kramer et al. |
| 5,180,371 A | 1/1993 | Spinello |
| 5,200,604 A | 4/1993 | Rudko et al. |
| 5,221,268 A | 6/1993 | Barton et al. |
| 5,271,413 A | 12/1993 | Dalamagas et al. |
| 5,300,029 A | 4/1994 | Denance |
| 5,318,522 A | 6/1994 | D'Antonio |
| 5,352,196 A | 10/1994 | Haber et al. |
| 5,354,286 A | 10/1994 | Mesa et al. |
| 5,354,287 A | 10/1994 | Wacks |
| 5,382,785 A | 1/1995 | Rink |
| 5,393,497 A | 2/1995 | Haber et al. |
| 5,425,715 A | 6/1995 | Dalling et al. |
| 5,451,210 A | 9/1995 | Kramer et al. |
| 5,456,670 A | 10/1995 | Neer et al. |
| 5,458,263 A | 10/1995 | Ciammitti |
| 5,478,316 A | 12/1995 | Bitdinger et al. |
| 5,540,664 A | 7/1996 | Wyrick |
| 5,569,190 A | 10/1996 | D'Antonio |
| 5,569,212 A | 10/1996 | Brown |
| 5,578,014 A | 11/1996 | Erez et al. |
| 5,584,815 A | 12/1996 | Pawelka et al. |
| 5,593,390 A | 1/1997 | Castellano et al. |
| 5,599,302 A | 2/1997 | Lilley et al. |
| 5,647,851 A | 7/1997 | Pokras |
| 5,665,071 A | 9/1997 | Wyrick |
| 5,681,291 A | 10/1997 | Galli |
| 5,690,618 A | 11/1997 | Smith et al. |
| 5,695,472 A | 12/1997 | Wyrick |
| 5,698,189 A | 12/1997 | Rowe et al. |
| 5,709,662 A | 1/1998 | Olive et al. |
| 5,720,729 A | 2/1998 | Kriesel |
| 5,728,074 A | 3/1998 | Castellano et al. |
| 5,746,714 A | 5/1998 | Salo et al. |
| 5,779,683 A * | 7/1998 | Meyer ................ A61M 5/2429 604/110 |
| 5,807,346 A | 9/1998 | Frezza |
| 5,843,036 A | 12/1998 | Olive et al. |
| 5,868,711 A | 2/1999 | Kramer et al. |
| 5,911,703 A | 6/1999 | Slate et al. |
| 5,919,159 A | 7/1999 | Lilley et al. |
| 5,921,963 A | 7/1999 | Erez et al. |
| 5,921,966 A | 7/1999 | Bendek et al. |
| 5,928,158 A | 7/1999 | Aristides |
| 5,945,046 A | 8/1999 | Hehl et al. |
| 5,957,897 A | 9/1999 | Jeffrey |
| 5,968,063 A | 10/1999 | Chu et al. |
| 6,019,745 A | 2/2000 | Gray |
| 6,019,747 A | 2/2000 | McPhee |
| 6,051,896 A | 4/2000 | Shibuya et al. |
| 6,099,503 A | 8/2000 | Stradella |
| 6,149,626 A | 11/2000 | Bachynsky et al. |
| 6,159,184 A | 12/2000 | Perez et al. |
| 6,171,276 B1 | 1/2001 | Lippe et al. |
| 6,171,283 B1 | 1/2001 | Perez et al. |
| 6,183,442 B1 | 2/2001 | Athanasiou et al. |
| 6,203,530 B1 | 3/2001 | Stewart, Sr. |
| 6,210,369 B1 | 4/2001 | Wilmot et al. |
| 6,213,987 B1 | 4/2001 | Hirsch |
| 6,241,709 B1 | 6/2001 | Bechtold et al. |
| 6,245,043 B1 | 6/2001 | Villette |
| 6,270,479 B1 | 8/2001 | Bergenset et al. |
| 6,280,421 B1 | 8/2001 | Kirchhofer et al. |
| 6,290,683 B1 | 9/2001 | Erez et al. |
| 6,344,030 B1 | 2/2002 | Duchon et al. |
| 6,344,032 B1 | 2/2002 | Perez et al. |
| 6,371,939 B2 | 4/2002 | Bergens et al. |
| 6,387,078 B1 | 5/2002 | Gillespie, III |
| 6,406,456 B1 | 6/2002 | Slate et al. |
| 6,447,482 B1 | 9/2002 | Ronborg et al. |
| 6,454,743 B1 | 9/2002 | Weber |
| 6,503,454 B1 | 1/2003 | Hadimioglu et al. |
| 6,520,928 B1 | 2/2003 | Junior |
| 6,540,672 B1 | 4/2003 | Simonsen et al. |
| 6,544,234 B1 | 4/2003 | Gabriel |
| 6,547,755 B1 | 4/2003 | Lippe et al. |
| 6,562,006 B1 | 5/2003 | Hjertman et al. |
| 6,569,127 B1 | 5/2003 | Fago et al. |
| 6,599,272 B1 | 7/2003 | Hjertman et al. |
| 6,641,561 B1 | 11/2003 | Hill et al. |
| 6,645,169 B1 | 11/2003 | Slate et al. |
| 6,645,177 B1 | 11/2003 | Shearn |
| 6,648,858 B2 | 11/2003 | Asbaghi |
| 6,652,483 B2 | 11/2003 | Slate et al. |
| D483,116 S | 12/2003 | Castellano |
| 6,656,163 B1 | 12/2003 | Marshall et al. |
| 6,656,164 B1 | 12/2003 | Smith |
| 6,669,664 B2 | 12/2003 | Slate et al. |
| 6,692,469 B1 | 2/2004 | Weekes et al. |
| 6,743,202 B2 | 6/2004 | Hirschman |
| 6,746,427 B2 | 6/2004 | Duchon et al. |
| 6,752,787 B1 | 6/2004 | Causey, III et al. |
| 6,767,336 B1 | 7/2004 | Kaplan |
| 6,770,052 B2 | 8/2004 | Hill et al. |
| 6,796,957 B2 | 9/2004 | Carpenter et al. |
| 6,805,686 B1 | 10/2004 | Fathallah et al. |
| 6,808,507 B2 | 10/2004 | Roser |
| 6,835,193 B2 | 12/2004 | Epstein et al. |
| 6,854,620 B2 | 2/2005 | Ramey |
| 6,890,319 B1 | 5/2005 | Crocker |
| 6,932,793 B1 | 8/2005 | Marshall et al. |
| 6,979,316 B1 | 12/2005 | Rubin et al. |
| 7,008,399 B2 | 3/2006 | Larsen et al. |
| 7,011,649 B2 | 3/2006 | De La Serna et al. |
| 7,025,774 B2 | 4/2006 | Freeman |
| 7,041,085 B2 | 5/2006 | Perez et al. |
| 7,066,909 B1 | 6/2006 | Peter et al. |

(56) References Cited

U.S. PATENT DOCUMENTS

| | | |
|---|---|---|
| 7,094,230 B2 | 8/2006 | Flaherty et al. |
| 7,104,400 B2 | 9/2006 | Kiehne |
| 7,118,553 B2 | 10/2006 | Scherer |
| 7,226,450 B2 | 6/2007 | Athanasiou et al. |
| 7,255,684 B2 | 8/2007 | Zubry |
| 7,273,469 B1 | 9/2007 | Chan et al. |
| 7,290,573 B2 | 11/2007 | Py et al. |
| 7,297,135 B2 | 11/2007 | Jeffrey |
| 7,297,136 B2 | 11/2007 | Wyrick |
| 7,357,790 B2 | 4/2008 | Hommann et al. |
| 7,361,160 B2 | 4/2008 | Hommann et al. |
| 7,370,759 B2 | 5/2008 | Hommann |
| 7,381,201 B2 | 6/2008 | Gilbert et al. |
| 7,390,319 B2 | 6/2008 | Friedman |
| 7,442,185 B2 | 10/2008 | Amark et al. |
| 7,449,012 B2 | 11/2008 | Young et al. |
| 7,476,217 B2 | 1/2009 | Martin et al. |
| 7,500,963 B2 | 3/2009 | Westbye et al. |
| 7,500,966 B2 | 3/2009 | Hommann |
| 7,553,294 B2 | 6/2009 | Lazzaro |
| 7,597,685 B2 | 10/2009 | Olson |
| 7,635,348 B2 | 12/2009 | Raven et al. |
| 7,635,350 B2 | 12/2009 | Scherer |
| 7,648,483 B2 | 1/2010 | Edwards et al. |
| 7,654,987 B2 | 2/2010 | Hommann et al. |
| 7,686,789 B2 | 3/2010 | Nemoto |
| 7,731,686 B2 | 6/2010 | Edwards et al. |
| 7,749,195 B2 | 7/2010 | Hommann |
| 7,760,099 B2 | 7/2010 | Knight |
| 7,785,292 B2 | 8/2010 | Harrison |
| 7,828,776 B2 | 11/2010 | Nemoto |
| D628,690 S | 12/2010 | Galbraith |
| 7,857,791 B2 | 12/2010 | Jacobs et al. |
| 7,887,513 B2 | 2/2011 | Nemoto |
| 7,901,377 B1 | 3/2011 | Harrison et al. |
| 7,909,796 B2 | 3/2011 | Weber |
| 7,918,823 B2 | 4/2011 | Edwards et al. |
| 7,922,695 B2 | 4/2011 | Wiegel et al. |
| 7,976,499 B2 | 7/2011 | Grunhut et al. |
| 8,012,125 B1 | 9/2011 | Fago et al. |
| 8,016,797 B2 | 9/2011 | Gratwohl et al. |
| 8,043,262 B2 | 10/2011 | Streit et al. |
| 8,048,037 B2 | 11/2011 | Kohlbrenner et al. |
| 8,052,645 B2 | 11/2011 | Slate et al. |
| D650,070 S | 12/2011 | Mori |
| 8,105,271 B2 | 1/2012 | Matusch |
| 8,141,417 B2 | 3/2012 | Gibson |
| 8,177,749 B2 | 5/2012 | Slate et al. |
| 8,226,610 B2 | 7/2012 | Edwards et al. |
| 8,277,414 B2 | 10/2012 | Barrow-Williams et al. |
| 8,298,171 B2 | 10/2012 | Ishikawa |
| 8,308,687 B2 | 11/2012 | Carrel et al. |
| 8,337,472 B2 | 12/2012 | Edginton |
| 8,343,103 B2 | 1/2013 | Moser |
| 8,376,985 B2 | 2/2013 | Pongpairochana et al. |
| 8,491,538 B2 | 7/2013 | Kohlbrenner et al. |
| 8,591,465 B2 | 11/2013 | Hommann |
| D694,879 S | 12/2013 | Julian et al. |
| 8,690,827 B2 | 4/2014 | Edwards et al. |
| 8,696,628 B2 | 4/2014 | Grunhut |
| 8,900,204 B2 | 12/2014 | Geertsen |
| 8,911,410 B2 | 12/2014 | Ekman et al. |
| 8,960,827 B2 | 2/2015 | McMillin et al. |
| 8,961,473 B2 | 2/2015 | Heald |
| 8,968,255 B2 | 3/2015 | Oakland |
| 9,011,386 B2 | 4/2015 | Kronestedt et al. |
| 9,138,542 B2 | 9/2015 | Smith |
| D748,783 S | 2/2016 | Zhang et al. |
| 9,278,177 B2 | 3/2016 | Edwards et al. |
| D757,254 S | 5/2016 | Wohlfahrt et al. |
| 9,616,173 B2 | 4/2017 | Slate et al. |
| 2001/0005781 A1* | 6/2001 | Bergens .............. A61M 5/2033 604/208 |
| 2001/0047153 A1 | 11/2001 | Trocki et al. |
| 2002/0022066 A1 | 2/2002 | Matsubayashi et al. |
| 2002/0095120 A1 | 7/2002 | Larsen et al. |
| 2002/0099334 A1 | 7/2002 | Hanson et al. |
| 2002/0133113 A1 | 9/2002 | Madsen et al. |
| 2002/0156426 A1 | 10/2002 | Gagnieux et al. |
| 2003/0036725 A1 | 2/2003 | Lavi et al. |
| 2003/0065536 A1 | 4/2003 | Hansen et al. |
| 2003/0105430 A1* | 6/2003 | Lavi .................. A61M 5/2033 604/136 |
| 2003/0236502 A1 | 12/2003 | De La Serna et al. |
| 2004/0039336 A1 | 2/2004 | Amark et al. |
| 2004/0054327 A1 | 3/2004 | Gillespie |
| 2004/0068266 A1 | 4/2004 | Delmotte |
| 2004/0116861 A1 | 6/2004 | Trocki et al. |
| 2004/0129803 A1 | 7/2004 | Dolder et al. |
| 2004/0133154 A1 | 7/2004 | Flaherty et al. |
| 2004/0133162 A1 | 7/2004 | Trocki et al. |
| 2004/0153008 A1 | 8/2004 | Sharf et al. |
| 2004/0225262 A1 | 11/2004 | Fathallah et al. |
| 2005/0020979 A1 | 1/2005 | Westbye et al. |
| 2005/0027255 A1 | 2/2005 | Lavi et al. |
| 2005/0033242 A1 | 2/2005 | Perez et al. |
| 2005/0049561 A1 | 3/2005 | Hommann et al. |
| 2005/0054987 A1 | 3/2005 | Perez et al. |
| 2005/0080377 A1 | 4/2005 | Sadowski et al. |
| 2005/0165404 A1 | 7/2005 | Miller |
| 2005/0171476 A1 | 8/2005 | Judson et al. |
| 2005/0171477 A1 | 8/2005 | Rubin et al. |
| 2005/0197650 A1 | 9/2005 | Sugimoto et al. |
| 2005/0203466 A1 | 9/2005 | Hommann et al. |
| 2005/0209569 A1 | 9/2005 | Ishikawa et al. |
| 2005/0261693 A1* | 11/2005 | Miller et al. ..................... 606/80 |
| 2005/0277885 A1 | 12/2005 | Scherer |
| 2006/0022363 A1 | 2/2006 | Konno et al. |
| 2006/0030819 A1 | 2/2006 | Young et al. |
| 2006/0157064 A1 | 7/2006 | Davison et al. |
| 2006/0173408 A1* | 8/2006 | Wyrick ............... A61M 5/2033 604/110 |
| 2006/0251646 A1 | 11/2006 | Utku |
| 2006/0270985 A1 | 11/2006 | Hommann et al. |
| 2007/0021720 A1 | 1/2007 | Guillermo |
| 2007/0027430 A1 | 2/2007 | Hommann |
| 2007/0066938 A1 | 3/2007 | Iio et al. |
| 2007/0100281 A1 | 5/2007 | Morris et al. |
| 2007/0112301 A1 | 5/2007 | Preuthun et al. |
| 2007/0112310 A1 | 5/2007 | Lavi et al. |
| 2007/0118081 A1 | 5/2007 | Daily et al. |
| 2007/0135767 A1 | 6/2007 | Gillespie et al. |
| 2007/0142787 A1 | 6/2007 | Scherer |
| 2007/0149925 A1 | 6/2007 | Edwards et al. |
| 2007/0167920 A1 | 7/2007 | Hommann |
| 2007/0173770 A1 | 7/2007 | Stamp |
| 2007/0197954 A1 | 8/2007 | Keenan |
| 2007/0197968 A1 | 8/2007 | Pongpairochana et al. |
| 2007/0219498 A1 | 9/2007 | Malone et al. |
| 2007/0233001 A1 | 10/2007 | Burroughs et al. |
| 2007/0239114 A1 | 10/2007 | Edwards et al. |
| 2007/0265568 A1 | 11/2007 | Tsals et al. |
| 2008/0039795 A1 | 2/2008 | Slate et al. |
| 2008/0051711 A1 | 2/2008 | Mounce et al. |
| 2008/0051714 A1 | 2/2008 | Moberg et al. |
| 2008/0051715 A1 | 2/2008 | Young et al. |
| 2008/0132841 A1 | 6/2008 | Chiwanga et al. |
| 2008/0140007 A1 | 6/2008 | Glynn |
| 2008/0262434 A1 | 10/2008 | Vaillancourt |
| 2008/0312602 A1 | 12/2008 | Barrow-Williams et al. |
| 2009/0018494 A1 | 1/2009 | Nemoto et al. |
| 2009/0018505 A1 | 1/2009 | Arguedas et al. |
| 2009/0024112 A1 | 1/2009 | Edwards et al. |
| 2009/0043253 A1 | 2/2009 | Podaima et al. |
| 2009/0149744 A1 | 6/2009 | Nemoto et al. |
| 2009/0254060 A1 | 10/2009 | Hetherington |
| 2009/0270622 A1 | 10/2009 | Fago |
| 2009/0292246 A1 | 11/2009 | Slate et al. |
| 2009/0312705 A1 | 12/2009 | Grunhut et al. |
| 2009/0322545 A1 | 12/2009 | Gibson |
| 2010/0016793 A1 | 1/2010 | Jennings et al. |
| 2010/0016795 A1 | 1/2010 | McLoughlin |
| 2010/0021456 A1 | 1/2010 | Miossec et al. |
| 2010/0022955 A1 | 1/2010 | Slate et al. |

(56) References Cited

U.S. PATENT DOCUMENTS

| | | |
|---|---|---|
| 2010/0036318 A1 | 2/2010 | Raday et al. |
| 2010/0152655 A1 | 6/2010 | Stamp |
| 2010/0152659 A1 | 6/2010 | Streit et al. |
| 2010/0160894 A1 | 6/2010 | Julian et al. |
| 2010/0198060 A1 | 8/2010 | Fago et al. |
| 2010/0268170 A1 | 10/2010 | Carrel et al. |
| 2010/0312195 A1 | 12/2010 | Johansen et al. |
| 2011/0004165 A1 | 1/2011 | Iio et al. |
| 2011/0023281 A1 | 2/2011 | Schraga |
| 2011/0044998 A1 | 2/2011 | Bedian et al. |
| 2011/0047153 A1 | 2/2011 | Betz |
| 2011/0092915 A1 | 4/2011 | Olson et al. |
| 2011/0097229 A1 | 4/2011 | Cauley, III et al. |
| 2011/0098655 A1 | 4/2011 | Jennings et al. |
| 2011/0137286 A1 | 6/2011 | Mudd et al. |
| 2011/0144594 A1 | 6/2011 | Sund et al. |
| 2011/0152781 A1 | 6/2011 | Brunnberg et al. |
| 2011/0160580 A1 | 6/2011 | Perkins et al. |
| 2011/0166512 A1 | 7/2011 | Both et al. |
| 2011/0184383 A1 | 7/2011 | Hasegawa |
| 2011/0190693 A1 | 8/2011 | Takatsuka et al. |
| 2011/0190702 A1 | 8/2011 | Stumber |
| 2011/0196339 A1 | 8/2011 | Hirschel et al. |
| 2011/0202011 A1 | 8/2011 | Wozencroft |
| 2011/0213315 A1 | 9/2011 | Sweeney et al. |
| 2011/0224616 A1 | 9/2011 | Slate et al. |
| 2011/0224620 A1 | 9/2011 | Johansen et al. |
| 2011/0224621 A1 | 9/2011 | Johansen et al. |
| 2011/0230833 A1 | 9/2011 | Landman et al. |
| 2011/0245761 A1 | 10/2011 | Jennings et al. |
| 2011/0257596 A1 | 10/2011 | Gaudet |
| 2011/0257604 A1 | 10/2011 | Banik |
| 2011/0264046 A1 | 10/2011 | Nyholm et al. |
| 2011/0270220 A1 | 11/2011 | Genosar |
| 2012/0035472 A1 | 2/2012 | Bruce et al. |
| 2012/0035538 A1 | 2/2012 | Elmen et al. |
| 2012/0056019 A1 | 3/2012 | Renz et al. |
| 2012/0059319 A1 | 3/2012 | Segal |
| 2012/0089119 A1 | 4/2012 | Slate et al. |
| 2012/0101439 A9 | 4/2012 | Slate et al. |
| 2012/0172815 A1 | 7/2012 | Holmqvist |
| 2012/0238961 A1 | 9/2012 | Julian et al. |
| 2012/0253314 A1 | 10/2012 | Harish et al. |
| 2012/0265142 A1 | 10/2012 | Slate et al. |
| 2012/0296286 A1 | 11/2012 | Raab et al. |
| 2012/0323176 A1 | 12/2012 | Watanabe et al. |
| 2013/0018313 A1 | 1/2013 | Kramer et al. |
| 2013/0018315 A1 | 1/2013 | Blomquist |
| 2013/0030383 A1 | 1/2013 | Keitel |
| 2013/0035647 A1 | 2/2013 | Veasey et al. |
| 2013/0046248 A1 | 2/2013 | Raab |
| 2013/0110054 A1 | 5/2013 | Raab et al. |
| 2013/0112521 A1 | 5/2013 | Ekman et al. |
| 2013/0131595 A1 | 5/2013 | Ekman et al. |
| 2013/0131601 A1 | 5/2013 | Pommereau et al. |
| 2013/0190719 A1 | 7/2013 | Smith et al. |
| 2013/0190721 A1 | 7/2013 | Kemp et al. |
| 2013/0204198 A1 | 8/2013 | Burnell et al. |
| 2013/0204204 A1 | 8/2013 | Butler et al. |
| 2013/0218092 A1 | 8/2013 | Davies et al. |
| 2013/0226091 A1 | 8/2013 | Nzike et al. |
| 2013/0261558 A1 | 10/2013 | Hourmand et al. |
| 2013/0274668 A1 | 10/2013 | Barrow-Williams et al. |
| 2013/0289491 A1 | 10/2013 | Kramer et al. |
| 2013/0310744 A1 | 11/2013 | Brereton et al. |
| 2013/0310761 A1 | 11/2013 | Plumptre |
| 2013/0317430 A1 | 11/2013 | Brereton et al. |
| 2013/0317480 A1 | 11/2013 | Reber et al. |
| 2013/0324935 A1 | 12/2013 | Brereton et al. |
| 2013/0338601 A1 | 12/2013 | Cowe |
| 2014/0046259 A1 | 2/2014 | Reber et al. |
| 2014/0257197 A1 | 9/2014 | Madsen et al. |
| 2014/0276448 A1 | 9/2014 | Muller-Pathle et al. |
| 2014/0296825 A1 | 10/2014 | Lemaire et al. |
| 2014/0303556 A1 | 10/2014 | Travanty |
| 2014/0330216 A1 | 11/2014 | Weaver et al. |
| 2014/0336590 A1 | 11/2014 | Hourmand et al. |
| 2014/0364808 A1 | 12/2014 | Niklaus et al. |
| 2015/0045729 A1 | 2/2015 | Denzer et al. |
| 2015/0080809 A1 | 3/2015 | Dasbach et al. |
| 2015/0136809 A1 | 5/2015 | Hamann et al. |
| 2015/0141923 A1 | 5/2015 | Wurmbauer et al. |
| 2015/0151046 A1 | 6/2015 | Nagel et al. |
| 2015/0165130 A1 | 6/2015 | Butler et al. |
| 2015/0217057 A1 | 8/2015 | Hogdahl |
| 2016/0022914 A1 | 1/2016 | Mounce et al. |
| 2016/0120751 A1 | 5/2016 | Mounce et al. |
| 2016/0271326 A1 | 9/2016 | Slate et al. |
| 2017/0043105 A1 | 2/2017 | Elmen |
| 2017/0157326 A1 | 6/2017 | Slate et al. |

FOREIGN PATENT DOCUMENTS

| | | |
|---|---|---|
| CA | 2074565 | 7/1992 |
| DE | 102007061775 A1 | 7/2009 |
| EP | 1227423 A1 | 7/2002 |
| ES | 2121536 A1 | 11/1998 |
| FR | 2390175 | 4/1976 |
| FR | 2581548 A1 | 11/1986 |
| FR | 2592307 A1 | 7/1987 |
| FR | 2622457 A1 | 5/1989 |
| FR | 2716375 A1 | 8/1995 |
| IL | 877559 A | 6/1993 |
| JP | S63139563 A | 6/1988 |
| JP | S63139563 A | 6/1988 |
| JP | 2008157 | 1/1990 |
| JP | H07503384 A | 4/1995 |
| JP | H07185000 A | 7/1995 |
| JP | 2001518366 A | 10/2001 |
| JP | 2002543931 A | 12/2002 |
| JP | 2003220142 A | 8/2003 |
| JP | 20020531228 A | 8/2004 |
| JP | 2005514082 A | 5/2005 |
| JP | 2006507061 A | 3/2006 |
| JP | 2006528040 A | 12/2006 |
| JP | 2007-500561 A | 1/2007 |
| JP | 2007111518 A | 5/2007 |
| JP | 2007529243 A | 10/2007 |
| JP | 2008508961 A | 3/2008 |
| JP | 2010511414 A | 4/2010 |
| WO | 8606967 A1 | 12/1986 |
| WO | 8703494 A1 | 6/1987 |
| WO | 8707160 A1 | 12/1987 |
| WO | 9118634 A1 | 12/1991 |
| WO | 9206725 A1 | 4/1992 |
| WO | 9208506 A1 | 5/1992 |
| WO | 9221392 A1 | 12/1992 |
| WO | 9302728 A1 | 2/1993 |
| WO | 9313817 A1 | 7/1993 |
| WO | 9324160 A1 | 12/1993 |
| WO | 9325256 A1 | 12/1993 |
| WO | 9406494 A1 | 3/1994 |
| WO | 9521645 A1 | 8/1995 |
| WO | 9525555 A1 | 9/1995 |
| WO | 9531235 A1 | 11/1995 |
| WO | 9534333 A2 | 12/1995 |
| WO | 9600594 A1 | 1/1996 |
| WO | 9621482 A2 | 7/1996 |
| WO | 9626754 A2 | 9/1996 |
| WO | 9638190 A1 | 12/1996 |
| WO | 9707839 A1 | 3/1997 |
| WO | 9731665 A1 | 9/1997 |
| WO | 9813077 A2 | 4/1998 |
| WO | 9817332 A2 | 4/1998 |
| WO | 9821408 A1 | 5/1998 |
| WO | 9917823 A1 | 4/1999 |
| WO | 9920327 A2 | 4/1999 |
| WO | WO-9917823 | 4/1999 |
| WO | 9921600 A2 | 5/1999 |
| WO | WO-99/65548 A1 | 12/1999 |
| WO | 0002605 A1 | 1/2000 |
| WO | 0009186 A2 | 2/2000 |
| WO | 0024441 A1 | 5/2000 |
| WO | 0025846 A2 | 5/2000 |

(56) References Cited

FOREIGN PATENT DOCUMENTS

| | | |
|---|---|---|
| WO | 0100261 A1 | 1/2001 |
| WO | 0137903 A2 | 5/2001 |
| WO | 0141835 A2 | 6/2001 |
| WO | 0189634 A2 | 11/2001 |
| WO | 0207812 A2 | 1/2002 |
| WO | WO-2002/11792 | 2/2002 |
| WO | 0249691 A2 | 6/2002 |
| WO | WO-2002/060513 A2 | 8/2002 |
| WO | 02092153 A2 | 11/2002 |
| WO | 03006099 A1 | 1/2003 |
| WO | 03008023 A1 | 1/2003 |
| WO | WO-03/008023 A1 | 1/2003 |
| WO | WO-2003/024385 A1 | 3/2003 |
| WO | WO-03/03934 A1 | 5/2003 |
| WO | 03047663 A2 | 6/2003 |
| WO | WO-2003/047659 A1 | 6/2003 |
| WO | 03090509 A2 | 11/2003 |
| WO | 03103749 A2 | 12/2003 |
| WO | WO-2004/004809 A1 | 1/2004 |
| WO | 2004069303 A2 | 8/2004 |
| WO | 2004108193 A1 | 12/2004 |
| WO | 2005053771 A2 | 6/2005 |
| WO | 2005070481 A1 | 8/2005 |
| WO | 2005079440 A2 | 9/2005 |
| WO | 2005089831 | 9/2005 |
| WO | 2005094923 A1 | 10/2005 |
| WO | 2006015501 A1 | 2/2006 |
| WO | 2006017732 A2 | 2/2006 |
| WO | 2006020609 A1 | 2/2006 |
| WO | 2006062788 A2 | 6/2006 |
| WO | 2006063015 A2 | 6/2006 |
| WO | 2006084821 A2 | 8/2006 |
| WO | 2006086774 A2 | 8/2006 |
| WO | 2007002053 A2 | 1/2007 |
| WO | 2007044980 A2 | 4/2007 |
| WO | 2007047200 A1 | 4/2007 |
| WO | 2007053779 A2 | 5/2007 |
| WO | 2007075677 A2 | 7/2007 |
| WO | WO-2007075677 A2 | 7/2007 |
| WO | 2007099044 A1 | 9/2007 |
| WO | 2007126851 A2 | 11/2007 |
| WO | 2007138299 A1 | 12/2007 |
| WO | 2007140610 A1 | 12/2007 |
| WO | WO-2007138313 A1 | 12/2007 |
| WO | 2008021776 A2 | 2/2008 |
| WO | 2008024810 A2 | 2/2008 |
| WO | 2008048750 A2 | 4/2008 |
| WO | 2008064092 A2 | 5/2008 |
| WO | 2008075033 A1 | 6/2008 |
| WO | 2008083313 A2 | 7/2008 |
| WO | 2008093063 A2 | 8/2008 |
| WO | 2008094984 A2 | 8/2008 |
| WO | 2008095124 A1 | 8/2008 |
| WO | WO-2008093063 A2 | 8/2008 |
| WO | 2008107670 A2 | 9/2008 |
| WO | 2008139458 A2 | 11/2008 |
| WO | 2008139460 A2 | 11/2008 |
| WO | 2008146021 A1 | 12/2008 |
| WO | 2009006725 A1 | 1/2009 |
| WO | 2009019437 A1 | 2/2009 |
| WO | 2009097325 A1 | 8/2009 |
| WO | 2009143255 A1 | 11/2009 |
| WO | 2010023481 A1 | 3/2010 |
| WO | 2010026414 A1 | 3/2010 |
| WO | WO-2010026414 A1 | 3/2010 |
| WO | 2010076275 A1 | 7/2010 |
| WO | 2010091133 A2 | 8/2010 |
| WO | 2010100213 A1 | 9/2010 |
| WO | WO-2010099850 A1 | 9/2010 |
| WO | 2010127449 A1 | 11/2010 |
| WO | 2011057065 A1 | 5/2011 |
| WO | 2012000871 A1 | 1/2012 |
| WO | 2012000940 A2 | 1/2012 |
| WO | WO-2012/103140 A1 | 8/2012 |
| WO | 2012145685 A1 | 10/2012 |
| WO | WO-2012145685 A1 | 10/2012 |
| WO | 2012164389 A2 | 12/2012 |
| WO | 2012164394 A2 | 12/2012 |
| WO | 2012164397 | 12/2012 |
| WO | 2013001378 A1 | 1/2013 |
| WO | WO-2013001378 A2 | 1/2013 |
| WO | 2013034984 | 3/2013 |
| WO | 2013034986 | 3/2013 |
| WO | 2013065055 A1 | 5/2013 |
| WO | 2014143815 A2 | 9/2014 |
| WO | 2014144096 A1 | 9/2014 |

OTHER PUBLICATIONS

Written Opinion of the International Searching Authority issued for International Application No. PCT/US09/44693 filed May 20, 2009 of Slate et al.
International Preliminary Report on Patentability of the International Searching Authority issued for International Application No. PCT/US09/44693 filed May 20, 2009 of Slate et al.
Notice of Allowance dated Apr. 6, 2011 issued in co-pending U.S. Appl. No. 12/178,447, filed Jul. 23, 2008 of Slate et al.
Notice of Allowance dated Jun. 24, 2011 issued in co-pending U.S. Appl. No. 12/178,447, filed Jul. 23, 2008 of Slate et al.
Office Action dated Oct. 15, 2009 issued in co-pending U.S. Appl. No. 12/178,447, filed Jul. 23, 2008 of Slate et al.
Office Action dated Mar. 30, 2010 issued in co-pending U.S. Appl. No. 12/178,447, filed Jul. 23, 2008 of Slate et al.
Office Action dated Dec. 22, 2010 issued in co-pending U.S. Appl. No. 12/178,447, filed Jul. 23, 2008 of Slate et al.
Notice of Allowance dated Oct. 3, 2011 issued in co-pending U.S. Appl. No. 12/123,888, filed May 20, 2008 of Slate et al.
Notice of Allowance dated Jan. 12, 2012 issued in co-pending U.S. Appl. No. 12/123,888, filed May 20, 2008 of Slate et al.
Office Action dated Oct. 5, 2009 issued in co-pending U.S. Appl. No. 12/123,888, filed May 20, 2008 of Slate et al.
Office Action dated Apr. 8, 2010 issued in co-pending U.S. Appl. No. 12/123,888, filed May 20, 2008 of Slate et al.
Office Action dated Dec. 22, 2010 issued in co-pending U.S. Appl. No. 12/123,888, filed May 20, 2008 of Slate et al.
Office Action dated Jun. 8, 2011 issued in co-pending U.S. Appl. No. 12/123,888, filed May 20, 2008 of Slate et al.
U.S. Appl. No. 13/269,750, filed Oct. 10, 2011, entitled, "System and Method for an Injection Using a Syringe Needle," of Slate et al.
U.S. Appl. No. 12/993,163, filed May 27, 2011, entitled, "Autoinjector System," of Slate et al.
"Related Australian Patent Application No. 2009 249027 Office Action", Jul. 24, 2013, Publisher: IP Australia, Published in: AU.
"Related European Patent Application No. EP 09 751 483.0", "Office Action", May 14, 2014, Publisher: EPO, Published in: EP.
"Related European Patent Application No. EP 09 75 1483 Office Action", Aug. 1, 2013, Publisher: EPO, Published in: EP.
"Related Japanese Patent Application No. JP 2011-510683 Office Action ", Jul. 30, 2013, Publisher: JPO, Published in: JP.
"Related Mexican Patent Application No. MX/a/20101012691", "Office Action", Feb. 10, 2014, Publisher: IInstituto Mexicano de la Propiedad Industrial, Published in: MX.
"Related U.S. Appl. No. 12/993,163 Non-Final Office Action", Dec. 27, 2013, Publisher: USPTO, Published in: U.S.
"Related U.S. Appl. No. 13/269,750 Final Office Action", Dec. 26, 2013, Publisher: USPTO, Published in: U.S.
"Related U.S. Appl. No. 13/269,740 Office Action", Jun. 21, 2013, Publisher: USPTO, Published in: U.S.
"Related International Application No. PCT/US2012/034535 International Preliminary Report on Patentability and Written Opinion of the ISA", Oct. 31, 2013, Publisher: PCT, Published in: CH.
"Related Japanese Patent Application No: JP 2011-510683", "Office Action", Jun. 30, 2014, Publisher: JPO, Published in: JP.
"Office Action", dated Jan. 5, 2015, issued in related Japanese Application JP2014-021052 (counterpart to U.S. Appl. No. 12/123,888).

(56) References Cited

OTHER PUBLICATIONS

"Notice of Acceptance," dated Aug. 7, 2014, issued in Australian Patent Application No. 2009249027, which is the counterpart to related copending U.S. Appl. No. 12/993,163.
"Office Action," dated Sep. 24, 2014, issued in Mexican Patent Application No. MX/a/2010/012691, which is the counterpart to related copending U.S. Appl. No. 12/993,163.
"Non-Final Office Action," dated Aug. 21, 2014, issued in related copending U.S. Appl. No. 13/269,750, Publisher: USPTO.
"International Search Report and Written Opinion," dated Oct. 7, 2014, issued in related International Patent Application No. PCT/US2014/027950, Publisher: WIPO.
"International Search Report and Written Opinion," dated Aug. 18, 2014, issued in related International Patent Application No. PCT/US2014/028363, Publisher: WIPO.
Michael Denzer et al., related copending U.S. Appl. No. 14/112,479, 371(c) dated Sep. 17, 2014.
"Non-Final Office Action," dated Sep. 11, 2014, issued in related copending U.S. Appl. No. 12/993,163, Publisher: USPTO.
"Office Action", dated Apr. 10, 2015, issued in European Patent Application No. 09751483.0 (counterpart to related U.S. Appl. No. 12/993,163).
"Final Office Action", dated Jun. 1, 2015, issued in Japanese Patent Application No. 2011-510683 (counterpart to related U.S. Appl. No. 12/993,163).
"Final Office Action", dated Apr. 20, 2015, issued in related Japanese Patent Application No. JP 2014-021052 (counterpart to related U.S. Appl. No. 12/993,163).
"Office Action", dated May 8, 2015, issued in related U.S. Appl. No. 12/993,163.
"Office Action", dated Mar. 8, 2015, issued in related U.S. Appl. No. 13/269,750.
"Extended European Search Report", dated Jul. 16, 2015, issued in European Patent Application No. 12774589 (counterpart to related U.S. Appl. No. 14/112,479).
"International Preliminary Report on Patentability", dated Oct. 22, 2013, issued in related International Application No: PCT/US2012/034535 (counterpart to related U.S. Appl. No. 14/112,479).
"EP Office Action" issued in European Patent Application No. 09 751 483.0, dated Nov. 16, 2015 (foreign counterpart of related U.S. Appl. No. 12/993,163).
"Non-Final Office Action" issued in related U.S. Appl. No. 13/269,750 dated Aug. 10, 2015.
"Final Office Action" issued in related U.S. Appl. No. 13/269,750 dated Nov. 18, 2015.
"Office Action" dated Nov. 23, 2015, issued in Canadian Application No. 2,833,748 (foreign counterpart of related U.S. Appl. No. 14/112,479).
"Office Action" issued in Japanese Patent Application No. 2014-506591 on Jan. 4, 2016 (foreign counterpart to related U.S. Appl. No. 14/112,479).
"Notice of Allowance, issued in Japanese Application No.; 2011-510683 (Foreign counterpart of U.S. Appl. No. 12/993,163)", Oct. 5, 2015.
"Notice of Allowance, issued in Japanese Continuation Application No: 2014-021052 (Foreign counterpart of U.S. Appl. No. 12/993,163)", Aug. 24, 2015.
William Byrne, "First Examination Report," dated Jun. 4, 2015, issued in counterpart Canadian Application No. 2,724,641.
Theodore J. Stigell, "Final Office Action," dated Nov. 18, 2015, issued in related U.S. Appl. No. 13/269,750.
Monica Lopez Garcia, "Extended European Search Report," dated Jul. 16, 2015, issued in related European Patent Application No. 12774589 (counterpart to related U.S. Appl. No. 14/112,479).
Matthew Engel, "Final Office Action" dated Feb. 22, 2016, issued in related U.S. Appl. No. 12/993,163.
Theodore J. Stigell, "Non Final Office Action" dated May 3, 2016, issued in related U.S. Appl. No. 13/269,750.

Timothy Williams, "First Examination Report" issued in Australian Patent Application No. 2012245231, dated Oct. 19, 2015 (Foreign counterpart to related U.S. Appl. No. 14/112,479).
William Tse, "Office Action", dated Nov. 23, 2015, issued in Canadian Application No. 2,833,748 (Foreign counterpart to U.S. Appl. No. 14/112,479).
Yukari Nakamura, "International Preliminary Report on Patentability" issued in PCT International Application No. PCT/US2014/027950 (International counterpart to related U.S. Appl. No. 14/777,255), dated Jun. 15, 2015.
Simin Baharlou, "International Preliminary Report on Patentability" issued in PCT International Application No. PCT/US2014/028363 (International counterpart to related U.S. Appl. No. 14/777,259), dated Sep. 15, 2015.
Michael Denzer et al., Related unpublished U.S. Appl. No. 29/548,507, filed Dec. 14, 2015.
Michael Denzer et al., Related unpublished U.S. Appl. No. 29/548,508, filed Feb. 14, 2015.
Office Action for Australian Patent Application No. 2014268140, dated Jul. 22, 2016.
Office Action for Japanese Application No. 2015-186876, dated Jul. 15, 2016.
"Office Action" issued in related Australian Patent Application No. 2012245231, dated Oct. 19, 2015 (Foreign counterpart to related U.S. Appl. No. 14/112,479).
"Office Action" issued in Japanese Patent Application No. 2014-506591 dated Jan. 4, 2016 (Foreign counterpart to related U.S. Appl. No. 14/112,479).
"Final Office Action, dated Apr. 20, 2015" issued in related Japanese Patent Application No. JP 2014-021052 (counterpart to related U.S. Appl. No. 12/993,163).
Office Action, dated Apr. 10, 2015, issued in European Patent Application No.: 097514830 (counterpart to related U.S. Appl. No. 12/993,163).
"Related European Patent Application No.: EP 09 751 483.0", "Office Action", May 14, 2014, Publisher: EPO, Published in: EP.
"Non-Final Office Action dated Apr. 21, 2015", issued in related U.S. Appl. No. 12/454,531, dated Apr. 21, 2015.
"Notice of Allowance", issued in related U.S. Appl. No. 13/454531 pri Oct. 5, 2015.
Related International Patent Application No: PCT/US2014/028363, filed Mar. 14, 2014, (International Application Publication No.: WO 2014/144096)
"Related U.S. Appl. No. 13/269,750 Office Action", dated Dec. 26, 2013. Publisher: USPTO. Published in: U.S.
"Related U.S. Appl. No. 13/269,740 Office Action", dated Jun. 21, 2013. Publisher: USPTO. Published in: U.S.
"Related International Application No. PCT/US2012/34535 International Search Report and Written Opinion", Aug. 17, 2012, Publisher: PCT. Published in: U.S.
U.S. Appl. No. 13/454,531, filed on Apr. 24, 2012, entitled, "Cassette for a Hidden Injection Needle," of SLATE et al.
"Notice of Allowance" issued in counterpart Australian Patent Application No. 2012245231, dated Oct. 4, 2016.
"Notice of Allowance" issued in counterpart Japanese Patent Application No. 2014-506591, dated Oct. 3, 2016.
"Office Action" issued in related Taiwan Patent Application No. 103109332, dated Aug. 22, 2016.
"Office Action" issued in related Taiwan Patent application No. 103109475, dated Aug. 26, 2016.
Australian patent application No. 2017200125, Examination Report No. 1, dated Sep. 18, 2017.
Canadian patent application No. 2833748, Examination Report, dated May 2, 2017.
Canadian patent application No. 2724641, Examination Report, dated Dec. 15, 2016.
Canadian patent application No. 2724641, Examination Report, dated Sep. 29, 2017.
Canadian patent application No. 2833748, Examination Report, dated Aug. 12, 2016.
European patent application No. 12774589.1, Extended Search Report, dated Feb. 23, 2015.

(56) References Cited

OTHER PUBLICATIONS

European patent application No. 14763010.7, Extended Search Report and Opinion, dated Jan. 10, 2017.
European patent application No. 14763010.7, Partial Supplementary Search Report dated Oct. 24, 2016.
European patent application No. 14765760.5, Extended Search Report, dated Jan. 11, 2017.
European patent application No. 14765760.5, Partial Supplementary Search Report, dated Oct. 24, 2016.
"Office Action", dated Mar. 12, 2015, issued in related U.S. Appl. No. 13/269,750.
"Office Action", dated Jun. 4, 2015, issued in related Canadian Patent Application No. 2724641.
"Office Action" issued in related Australian Patent Application No. 2014268139, dated Jul. 19, 2016.
"Non-Final Office Action" issued in related U.S. Appl. No. 12/993,163, dated Jul. 28, 2016.
"Final Office Action" dated Oct. 18, 2016 issued related U.S. Appl. No. 13/269,150.
"Office Action" issued in counterpart Australian Patent Application No. 2012245231, dated Jul. 5, 2016.
"Office Action" issued in counterpart Canadian Patent Application No. 2833748, dated Aug. 12, 2016.
Extended European Search Report for Application No. 14763010.7, dated Jan. 10, 2017.
Japanese patent application No. 2015-171851, Decision of Rejection (English translation), dated Feb. 6, 2017.
Japanese patent application No. 2016-214237, Notice of Reasons for Rejection (English translation), dated Sep. 4, 2017.
"Office Action" issued In related European Patent Application No. 9751483.0, dated Aug. 1, 2016.
Unpublished related design U.S. Appl. No. 29/548,507.
Unpublished related design U.S. Appl. No. 29/548,508.
Unpublished related design U.S. Appl. No. 14/777,255.
U.S. Appl. No. 13/269,750, Final Office Action, dated Oct. 18, 2016.
U.S. Appl. No. 13/269,750, Notice of Allowance, dated Feb. 8, 2017.
U.S. Appl. No. 14/112,479, Final Office Action, dated Feb. 27, 2017.
U.S. Appl. No. 14/112,479, Nonfinal Office Action, dated Jul. 12, 2017.
U.S. Appl. No. 14/112,479, Nonfinal Office Action, dated Jul. 29, 2016.

* cited by examiner

CASSETTE FOR A HIDDEN INJECTION NEEDLE

RELATED APPLICATION

This application is a continuation of co-pending U.S. application Ser. No. 12/123,888, filed on May 20, 2008. The entire disclosure of U.S. application Ser. No. 12/123,888 is incorporated herein by reference.

FIELD OF THE INVENTION

The present invention pertains generally to systems for injecting fluid medicaments into a patient from a pre-filled hypodermic syringe. More particularly, the present invention pertains to systems wherein the needle of the hypodermic syringe remains concealed and hidden during an injection procedure. The present invention is particularly, but not exclusively, useful as a system wherein a hypodermic syringe is concealed in a cassette; wherein the cassette is engageable with a drive mechanism; and wherein the drive mechanism uses one motor to present the syringe needle for an injection, and uses another motor to expel fluid medicament through the syringe needle.

BACKGROUND OF THE INVENTION

Pre-filled hypodermic syringes provide several advantages for the home-use market. These advantages include the fact that pre-filled syringes can be prepared for each fluid medicament with the exactly required dosage. Further, they are easily operated, by merely advancing the stopper of the syringe. Aside from the costs of the particular medication that is being used, pre-filled syringes are also economically manufactured. A consequence of all this is that pre-filled syringes have commercial appeal. Nevertheless, prefilled syringes also have a significant drawback in the marketplace. Specifically, many users are either frightened by an exposed needle or feel they are inherently incapable of performing an injection.

Because of aversions to exposed needles, as well as the many health and safety issues that may be involved, various needleless injectors and other devices have been developed for the specific purpose of concealing needles from the user. Typically, for devices where hidden or protected needles are employed, the devices are spring-operated and tend toward the use of cartridges, rather than the use of pre-filled hypodermic syringes. For example, U.S. Pub. No. 2007/0021720A1 which was filed for an invention entitled "Injector", discloses such a device employing a variety of spring activated mechanisms. When springs are employed, however, the forces cannot be varied from application to application. This can be particularly problematic in situations where it may be desirable to use a same device, at different times, to inject different medications, with different fluid viscosities. Indeed, it may not be possible to use a same spring-loaded injector for different medications. The situation can become further complicated when consideration is given to the fact that, in a single injection procedure, the optimal force for inserting a syringe needle into a patient may be quite different from the force required to subsequently expel fluid medicament from the syringe. Furthermore, the starting force of a spring will differ from the ending force. And, this can be problematic for assuring a complete drug delivery.

In light of the above, it is an object of the present invention to provide a system using disposable cassettes that are pre-loaded with pre-filled syringes to hide the syringe needle during its use. Another object of the present invention is to provide a system for injecting fluid medicaments into a patient that uses different motors to accommodate different force requirements during an injection procedure. Still another object of the present invention is to provide a system for injecting a fluid medicament to a patient that is easy to assemble, is simple to use, and is comparatively cost effective.

SUMMARY OF THE INVENTION

In accordance with the present invention, a system for injecting fluid medicaments into a patient from a pre-filled hypodermic syringe, employs a cassette that is pre-loaded with the pre-filled syringe. For this combination, the hypodermic syringe can be loaded into the cassette during manufacture, or be subsequently loaded by a contract service provider. In either case, the syringe needle is concealed inside the cassette and hidden from the view of the end-user. Importantly, the only preparation required by the end-user (e.g. the patient that is to self-administer the fluid medicament) is to mount the cassette onto a drive mechanism.

Structurally, the system of the present invention envisions a pre-filled syringe that will have a needle, and it will have a stopper for expelling the fluid medicament from the syringe through the needle. Further, the pre-filled syringe will be firmly held on the cassette in a position where the syringe needle is concealed and hidden from view. As envisioned for the present invention, the pre-filled hypodermic syringe can be firmly held in the concealed position, in any of several different ways. These include, the use of a latching mechanism, an adhesive, or a flexible abutment.

Once the cassette has been loaded with the pre-filled hypodermic syringe, the cassette can be engaged with a drive mechanism. In detail, the drive mechanism includes two separate motors that perform two different functions. A first motor is provided for engaging the syringe in its concealed position where its needle is hidden. With this engagement, the first motor then moves the syringe and its needle from the concealed position and into an exposed position where the needle is extended for insertion into the patient. While the needle is inserted into the patient, a second motor is provided for pushing the stopper on the syringe to expel fluid medicament from the syringe. After the injection has been completed, the first motor then withdraws the syringe and its needle back into the concealed position. Importantly, after it has been withdrawn the syringe is again firmly held in the concealed position, inside the cassette. Thus, the needle remains hidden from view at all times during an injection procedure. Further, as noted above, the syringe is firmly held inside the cassette to insure the syringe needle does not inadvertently extend from the cassette.

In operation, an end-user mounts a pre-loaded cassette on the drive mechanism. The end-user then removes a protective cover from the syringe needle and positions the system at a site where an injection is to be made. A button on the system is then pushed to activate the drive mechanism for an injector procedure. After the injection has been completed, the cassette, with its now empty syringe, can be removed from the drive mechanism and discarded.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
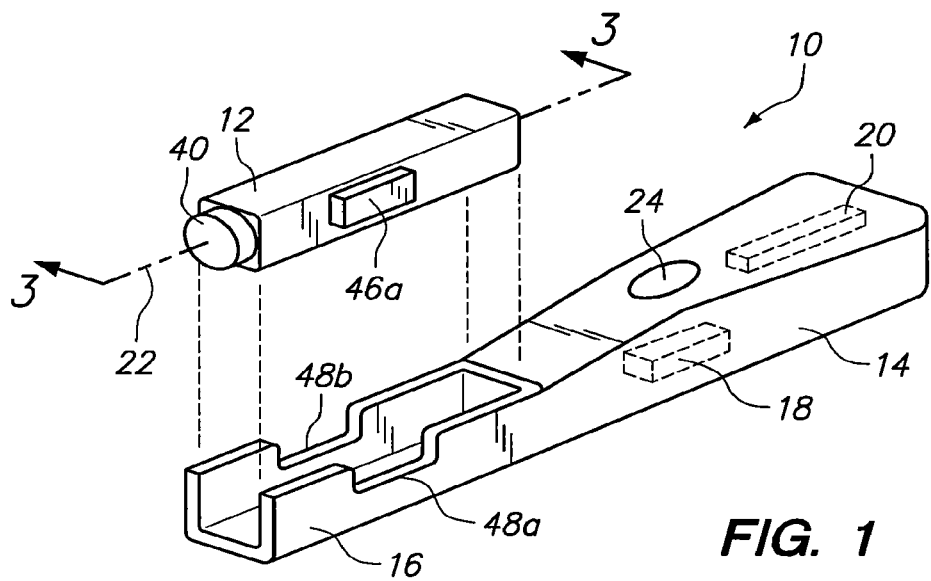
FIG. 1 is a perspective view of a cassette and associated drive mechanism for a system of the present invention.

Referring initially to FIG. 1, a system for injecting a fluid medicament into a patient is shown and is generally designated 10. In detail, FIG. 1 shows the system 10 includes a cassette 12 and a drive mechanism 14. Further, the drive mechanism 14 is formed with a cradle 16 that is dimensioned to receive and hold the cassette 12 on the drive mechanism 14. It is also indicated in FIG. 1 that the drive mechanism 14 includes a first motor 18 (shown in phantom) and a second motor 20 (also shown in phantom). For purposes of the present invention, the motors 18 and 20 can be of any standard type well known in the art (e.g. a lead screw). More specifically, the motors 18 and 20 must be capable of individually exerting axially directed forces on contents of the cassette 12. These forces will need to be directed substantially along the axis 22. Activation of the motors 18 and 20 for the generation of these forces is accomplished by manipulation of the button 24.

Figure 2:
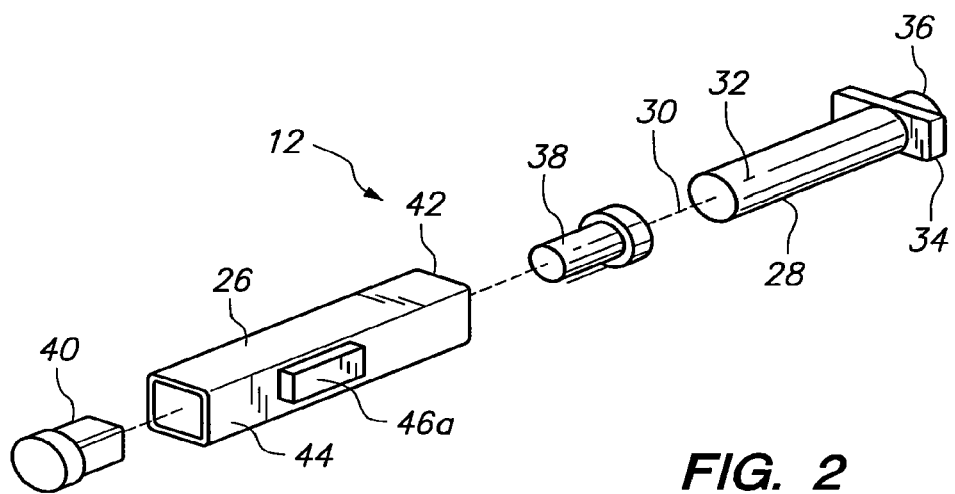
FIG. 2 is an exploded perspective view of the cassette with a pre-loaded, pre-filled hypodermic syringe.
Figure 3A:
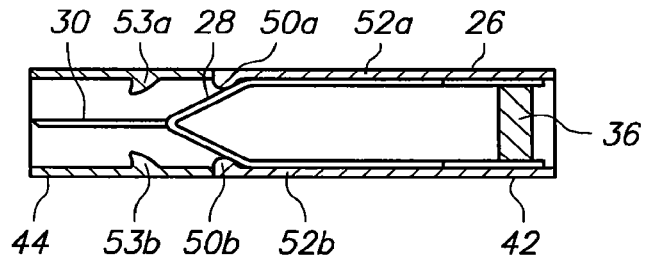
FIG. 3A is a cross-sectional view of a pre-loaded cassette, as seen along the line 3-3 in FIG. 1, with a pre-filled hypodermic syringe in a withdrawn (proximal) position.
Figure 3B:
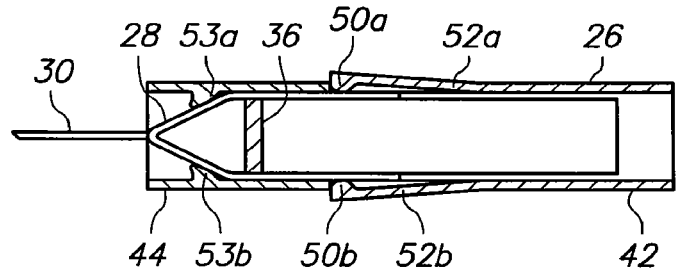
FIG. 3B is a view of the cassette shown in FIG. 3A with the syringe in an extended (distal) position after drug delivery.

Structurally, the cassette 12 and its interaction with associated contents are shown in FIG. 2. There it will be seen that the cassette 12 is essentially a housing 26 having hollow, tubular shaped structure. Importantly, the housing 26 is provided to hold a hypodermic syringe 28 having a needle 30 that is affixed to the distal end of its fluid chamber 32. A standard grip 34 is provided at the proximal end of the fluid chamber 32. Also, a stopper 36 is provided to expel fluid medicament from the fluid chamber 32 through the needle 30. A protective cover 38 can be provided to cover the needle 30 when system 10 is not in operational use, and a cap 40 is employed to grip the protective cover 38. Prior to an operation of the system 10, the cassette 12 is pre-loaded. And, furthermore, the syringe 28 is pre-filled with an appropriate dose of the desired fluid medicament. Before pre-loading the cassette 12, the protective cover 38 is positioned over the needle 30 on syringe 28. The pre-filled syringe 28 is then inserted into the housing 26 through its proximal end 42. The cap 40 can then be inserted through the distal end 44 of the housing 26 to engage the cap 40 with the protective cover 38. The cassette 12 is thus pre-loaded, and it will appear substantially as shown in FIG. 1. Once it has been pre-loaded, the cassette 12 can be mounted on the drive mechanism 14 is indicated in FIG. 1. This is done by merely inserting the cassette 12 into cradle 16. During this insertion the protrusions 46a and 46b (protrusion 46b is not shown) engage with respective recesses 48a and 48b to stabilize the cassette 12 on drive mechanism 14. An important structural aspect of the present invention is that when the pre-filled syringe 28 has been pre-loaded into the cassette 12, it will thereafter be firmly held inside the cassette 12. Specifically, it will be held in a position where the needle 30 is concealed inside the cassette 12 and thereby hidden from view. For example, FIG. 3A shows a syringe 28 being held in the housing 26 of a cassette 12 by opposed bumps 50a and 50b that are formed onto respective resilient arms 52a and 52b. While syringe 28 is in the position shown in FIG. 3A (sometimes referred to hereinafter as the concealed position or proximal position), the syringe needle 30 is hidden inside the housing 26. Also, until, the bumps 50a and 50b have been overcome by an axial force exerted by the syringe 28 and supplied by the first motor 18, the syringe 28 will be firmly held in its concealed position. FIG. 3B then shows that when a sufficient force has been applied by the first motor 18, the syringe 28 will move from its concealed (proximal) position, and into an extended (distal) position. In this distal position, the syringe 28 is retained in the cassette 12 by stops 53a and 53b while the needle 30 extends from the housing 26 for insertion into a patient. Importantly, the first motor 18 is attached to the syringe 28 in a manner that allows the first motor 18 to retract the syringe 28 from the extended (distal) position, and thereby return the needle 30 to its concealed (proximal) position. Again, the syringe 28 will be firmly held on the housing 26 by the bumps 50a and 50b.

Although the disclosure for the present invention is directed primarily toward a dual motor system (i.e. first motor 18 and second motor 20), two motors may not be necessary. Indeed, it will be readily appreciated by a person skilled in the art that a single motor may suffice for purposes of the present invention. In such a case, however, an appropriate transmission will be required for alternating between creating forces directly on the syringe 28 or on the stopper 36. In any event, the importance of using motors for system 10, vis-a-vis springs, is to generate controllable and reliable forces for movements of the syringe 28, or for expelling fluid medicament therefrom.

Figure 4:
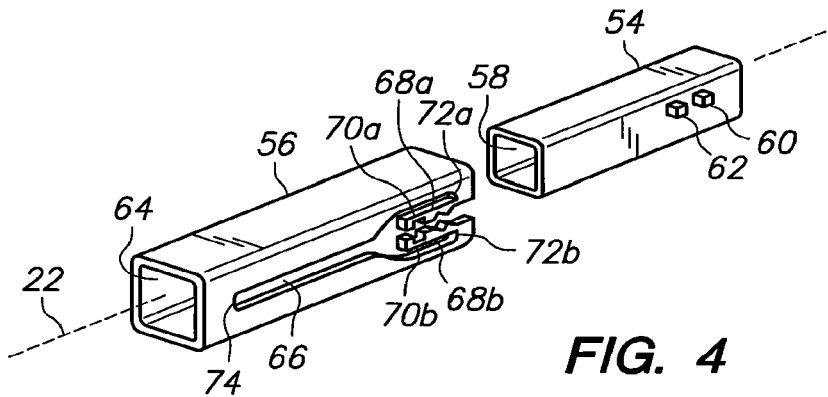
FIG. 4 is an exploded perspective view of another embodiment of a cassette for use with the present invention.

An alternate construction for the cassette 12 is shown in FIG. 4. There an embodiment for the cassette 12 is seen that includes an inner sleeve 54 and an outer sleeve 56. More specifically, the inner sleeve 54 is a hollow, substantially tube-shaped structure that is formed with a lumen 58. Formed onto the outside of the inner sleeve 54 are a proximal projection 60 and a distal projection 62 that are axially aligned with each other. FIG. 4 also shows that the outer sleeve 56, like inner sleeve 54, is hollow and substantially tube-shaped. Further, the outer sleeve 56 is formed with a lumen 64 and an axially aligned slot 66. Resilient arms 68a and 68b are formed on the outer sleeve 56 and are positioned to extend in the slot 66, substantially as shown. Additionally, the resilient arms 68a and 68b are respectively formed with detents 70a and 70b and ramps 72a and 72b.

Figure 6:
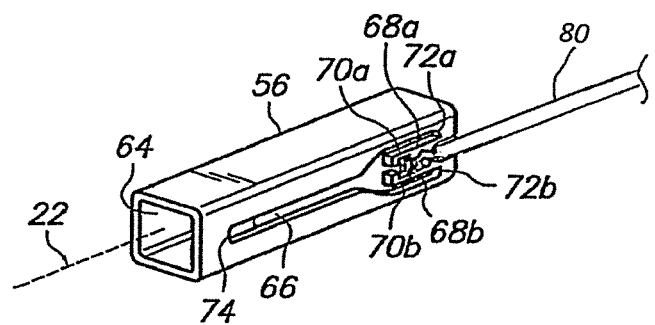
FIG. 6 is an assembled perspective view of the cassette shown in FIG. 4.

Referring to FIG. 6, in order to load a cassette 12 having the embodiment shown in FIG. 4, the inner sleeve 54 is inserted into the lumen 64 of the outer sleeve 56. Importantly, with this insertion the proximal projection 60 on inner sleeve 54 is positioned and held in the detents 70a and 70b of the arms 68a and 68b. The hypodermic syringe 28 can then be inserted into the lumen 58 of the inner sleeve 54. This places the syringe 28 in its concealed (proximal) position on 15 the cassette 12. Subsequently, movement of the syringe 28 from its concealed (proximal) position to its extended (distal) position is accomplished by the first motor 18. More specifically, a bar 80 which is operated by the first motor 18, is used to urge against the ramps 72a and 72b on arms 68a and 68b. This causes the arms 68a and 68b to spread and thereby 20 release the proximal projection 60 from their grasp. The inner sleeve 54, with syringe 28 firmly held thereon, can then be moved in a distal direction through the lumen 64 of the outer sleeve 56. This distal movement continues until the distal projection 62 contacts the end abutment 74 of the slot 66. The syringe 28 is now in its extended (distal) position. Subsequently, the first motor 18 can withdraw the inner sleeve 54 in a proximal direction through the lumen 64 of the outer sleeve 56. This proximal movement continues until the proximal projection 60 on inner sleeve 54 again engages with the detents 70a and 70b. Thus, the syringe 28 is returned to its concealed (proximal) position inside the cassette 12.

Figure 5:
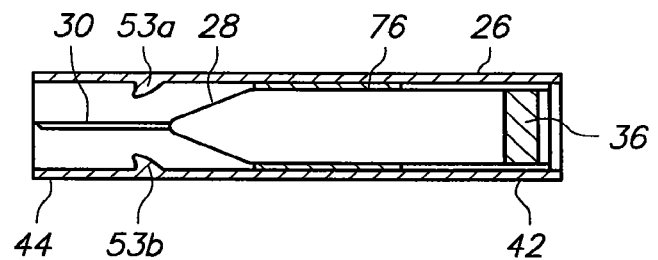
FIG. 5 is a cross-sectional view of an alternate embodiment of a preloaded cassette, as seen along the line 3-3 in FIG. 1.

FIG. 5 shows yet another embodiment for the cassette 12 of the present invention wherein an adhesive 76 is positioned on the cassette 12 to firmly hold the syringe 28 in its concealed (proximal) position. The adhesive 76, or a similar type of restraining element, can be used either directly between the syringe 28 and cassette 12 as shown in FIG. 5, or in some arrangement between the inner sleeve 54 and outer sleeve 56 when an embodiment as shown in FIG. 4 is employed. Alternatively, an arrangement such as disclosed in FIGS. 3A and 3B can also be used for an embodiment as shown in FIG. 4. The import here is that for an embodiment for the cassette 12 having an inner sleeve 54 and an outer sleeve 56, a structure other than the arms 68a and 68b can be used. In particular, an adhesive 76 or bumps 50a,b can be used in lieu of the arms 68a and 68b to hold the syringe 28 in its concealed (proximal) position.

In the operation of the system of the present invention, a pre-loaded cassette 12 is positioned in the cradle 16 on the drive mechanism 14. This engages the syringe 28 with the drive mechanism 14. Prior to an injection, the cap 40 is removed from the system 10. More specifically, because the cap 40 is attached to the protective cover 38 over needle 30 of the syringe 28, the protective cover 38 is also removed. The system 10 is now ready for an injection. With the system 10 positioned at an injection site (not shown), the button 24 on drive mechanism 14 is depressed. Depression of the button 24 causes the first motor 18 to engage with the syringe 28 and to move the syringe 28 from its concealed (proximal) position to its extended (distal) position. This causes the needle 30 of syringe 28 to penetrate into tissue of the patient for an injection. At this point, the second motor 20 pushes on stopper 36 to expel fluid medicament from the fluid chamber 32 of the syringe 25 28. After an injection has been completed, the first motor 18 is again activated. This time, however, instead of advancing the syringe 28, it withdraws the syringe 28 from the extended (distal) position to the concealed (proximal) position. The cassette 12, along with the expended syringe 28, can then be removed from the drive mechanism 14 and discarded.

While the particular Cassette for a Hidden Injection Needle as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for injecting a fluid medicament into a patient which comprises:
a motorized drive mechanism;
a hypodermic syringe with a needle, wherein the syringe is pre-filled with the fluid medicament and the syringe includes a stopper for expelling the medicament from the syringe through the needle;
a cassette for receiving and holding the hypodermic syringe, the syringe movable relative to the cassette between a first position and a second position, the cassette comprising an inner sleeve for holding the syringe, an outer sleeve for supporting the inner sleeve, the inner sleeve moveable relative to the outer sleeve between the first position and the second position, and a detent formed by the outer sleeve for retaining the syringe in the first position; and
a bar operated by the motorized drive mechanism for releasing the detent;
wherein the needle is concealed inside the cassette in the first position, and wherein the needle extends from the cassette in the second position for injection of the medicament.

2. A system as recited in claim 1 wherein the motorized drive mechanism comprises:
a first motor for moving the syringe between the first and the second positions; and
a second motor for pushing the stopper to expel the medicament from the syringe while the syringe is in one of the first and second positions.

3. A system as recited in claim 1 wherein the outer sleeve is a hollow tube having a wall defining an axis, and having a first end and a second end, with the wall of the tube having a longitudinal slot extending between the first and second ends of the tube, and wherein the cassette further comprises:
a resilient arm formed on the wall of the outer sleeve with a the detent formed on the arm, the arm being biased to extend the detent into the slot of the outer sleeve; and
a projection extending radially outward from the inner sleeve and into the slot of the outer sleeve for selective engagement with the detent of the outer sleeve.

4. A system as recited in claim 3 further comprising a pair of resilient arms, wherein the arms are opposite each other across the slot for concerted engagement with the projection on the inner sleeve.

5. A system as recited in claim 1 further comprising:
a protective cover positioned over the needle of the syringe; and
a cap engageable with the protective cover for subsequent removal of the protective cover with the cap when the cap is removed from the outer sleeve.

6. A system for injecting a fluid medicament into a patient, the system comprising:
a hypodermic syringe, wherein the syringe has a needle and a stopper for expelling the medicament from the syringe through the needle, and wherein the syringe is engaged with a cassette to conceal the needle of the syringe, the cassette comprising an inner sleeve for holding the syringe, an outer sleeve for supporting the inner sleeve, and a detent formed by the outer sleeve for retaining the syringe to conceal the needle;
a housing removeable engaging the cassette while the needle of the syringe is in a concealed position inside the cassette;

a first motor mounted on the housing for moving the syringe and its needle on the cassette from the concealed position to an extended position where the needle is exposed; and a second motor mounted on the housing for pushing the stopper to expel the medicament from the syringe while the syringe needle is in the extended position; and a bar operated by the first motor for releasing the detent.

7. A system for injecting a fluid medicament, the system comprising:

a disposable cassette containing a syringe prefilled with a fluid medicament, the cassette comprising a detent for retaining the syringe in a needle concealed position; and an injector comprising a cradle and a motorized drive mechanism, the cradle for receiving and holding the cassette and the motorized drive mechanism for releasing the detent and for causing the syringe to move in the cassette between the needle concealed position and a needle extended position.

8. A system as recited in claim 7 wherein the syringe comprises a stopper and the motorized drive mechanism comprises:

a first motor for moving the syringe in the cassette between the needle concealed and the needle extended positions; and a second motor for pushing the stopper to expel the medicament from the syringe if the syringe is in the needle extended position.

9. A system as recited in claim 7 wherein the cassette further comprises:

an outer sleeve; and an inner sleeve for holding the syringe, the inner sleeve movable within the outer sleeve between first and second positions;

wherein the syringe is in the needle concealed position when the inner sleeve is in the first position and the syringe is in the needle extended position when the inner sleeve is in the second position.

10. A system as recited in claim 9 wherein the detent is formed by the outer sleeve.

11. A system as recited in claim 9 wherein the outer sleeve comprises a wall, the wall having a slot and a first resilient arm with the detent, wherein the inner sleeve comprises a projection that engages the detent when the inner sleeve is in the first position, the projection being released from the detent by the motorized drive mechanism and traveling in the slot as the motorized drive mechanism moves the inner sleeve from the first position to the second position.

12. A system as recited in claim 11 wherein the projection re-engages the detent as the motorized drive mechanism moves the inner sleeve from the second position to the first position.

13. A system as recited in claim 11 wherein the detent comprises a first detent and wherein the wall of the outer sleeve has a second resilient arm with a second detent, wherein the projection engages the second detent when the inner sleeve is in the first position, the projection being released from the second detent by the motorized drive mechanism.

14. A system as recited in claim 13 wherein the projection re-engages the first and second detents as the motorized drive mechanism moves the inner sleeve from the second position to the first position.

15. A disposable cassette for use with an injector, the cassette comprising:

an outer sleeve;

an inner sleeve movable within the outer sleeve between first and second positions;

a syringe held by the inner sleeve, the syringe prefilled with a fluid medicament, wherein the syringe is in a needle concealed position when the inner sleeve is in the first position and the syringe is in a needle extended position when the inner sleeve is moved to the second position by a motorized drive mechanism of the injector; and a detent formed by the outer sleeve for retaining the inner sleeve in the first position, the detent being releasable by the motorized drive mechanism.

16. A disposable cassette as recited in claim 15 wherein the outer sleeve further comprises a wall, the wall having a slot and a first resilient arm with the detent, wherein the inner sleeve comprises a projection that engages the detent when the inner sleeve is in the first position, the projection being released from the detent by the motorized drive mechanism and traveling in the slot as the motorized drive mechanism moves the inner sleeve from the first position to the second position.

17. A disposable cassette as recited in claim 16 wherein the projection re-engages the detent as the motorized drive mechanism moves the inner sleeve from the second position to the first position.

18. A disposable cassette as recited in claim 16 wherein the detent comprises a first detent and wherein the wall of the outer sleeve has a second resilient arm with a second detent, wherein the projection engages the second detent when the inner sleeve is in the first position, the projection being released from the second detent by the motorized drive mechanism.

19. A disposable cassette as recited in claim 18 wherein the projection re-engages the first and second detents as the motorized drive mechanism moves the inner sleeve from the second position to the first position.

20. A system for injecting a fluid medicament comprising:

a cassette for concealing a hypodermic syringe, the syringe movable relative to the cassette, the syringe having a needle that is concealed inside the cassette if the syringe is in a first position relative to the cassette, the needle extending from the cassette if the syringe is in a second position relative to the cassette, the cassette comprising a detent for preventing movement of the syringe relative to the cassette; and a motorized drive mechanism, wherein the motorized drive mechanism is operative for releasing the detent, and wherein the cassette comprises:

an inner sleeve for holding the syringe; and an outer sleeve for supporting the inner sleeve, the inner sleeve moveable relative to the outer sleeve between the first position and & the second position, wherein the detent is formed by the outer sleeve.

21. A system as recited in claim 20 wherein the outer sleeve comprises a slot and a resilient arm, wherein the detent is formed on the resilient arm, and wherein the inner sleeve comprises a projection that extends into the slot of the outer sleeve and engages the detent when the sleeve is in the first position.

22. A system as recited in claim 20 wherein the outer sleeve is a hollow tube having a wall defining an axis, and having a first end and a second end, with the wall of the tube having a longitudinal slot extending between the first and second ends of the tube, and wherein the cassette further comprises:

a resilient arm formed on the wall of the outer sleeve with the detent formed on the arm, the arm being biased to extend the detent into the slot of the outer sleeve; and a projection extending radially outward from the inner sleeve and into the slot of the outer sleeve for selective engagement with the detent of the outer sleeve.

\* \* \* \* \*